US005834485A

United States Patent [19]
Dyke et al.

[11] Patent Number: 5,834,485
[45] Date of Patent: Nov. 10, 1998

[54] QUINOLINE SULFONAMIDES AND THEIR THERAPEUTIC USE

[75] Inventors: Hazel Joan Dyke; John Gary Montana, both of Cambridge, United Kingdom

[73] Assignee: Chiroscience Limited, United Kingdom

[21] Appl. No.: 858,969

[22] Filed: May 20, 1997

[30] Foreign Application Priority Data

| May 20, 1996 | [GB] | United Kingdom | 9610506 |
| Nov. 7, 1996 | [GB] | United Kingdom | 9623234 |
| Dec. 24, 1996 | [GB] | United Kingdom | 9626883 |
| Apr. 22, 1997 | [GB] | United Kingdom | 9708071 |

[51] Int. Cl.$^6$ ............... C07D 215/36; A61K 31/47
[52] U.S. Cl. ............... 514/311; 514/312; 514/313; 514/314; 546/153; 546/155; 546/156; 546/157; 546/159; 546/160; 546/168; 546/169; 546/170; 546/172
[58] Field of Search ............... 546/154, 155, 546/156, 157, 160, 162, 172; 514/311, 312, 313, 314

[56] References Cited

U.S. PATENT DOCUMENTS

| 5,340,811 | 8/1994 | Kajihara et al. ............... 514/253 |
| 5,571,821 | 11/1996 | Chan et al. ............... 514/312 |

FOREIGN PATENT DOCUMENTS

| 9422852 | 10/1994 | WIPO . |
| 9503051 | 2/1995 | WIPO . |
| 9636611 | 11/1996 | WIPO . |

OTHER PUBLICATIONS

Kajiwara et al. (1992) "Preparation of quinolinesulfonamide or isoquinolinesulfonamide derivatives as bronchodilators" Chemical Abstracts 116(2), abstract No. 128690f (abstract).
Thompson et al. (1957) "Antiamebic action of 5–chloro–7–diethylaminomethyl–8–quinolinol and of other substituted 8–quinolinols in vitro and in experimental animals" Chemical Abstracts 51(3) abstract No. 15005a3 (abstract).
Damasio et al., Alzheimer's Disease and related dementias, Cecil Textbook of Medicine, pp. 1992–1996, 1996.
Ibrahim et al., CA 122:95157, 1995.
Awad et al., CA 119:249886, 1993.
Abdel Hafez, CA 118:59668, 1993.
Ao et al., CA 114:6308, 1991.
Tochilkin et al., CA 113:164723, 1990.
Oki, CA 106:129242, 1987.
Tiwari et al., CA 100:60857, 1984.
Rottendorf, CA 64:19551e, 1966.

*Primary Examiner*—Mukund J. Shah
*Assistant Examiner*—Deepak R. Rao
*Attorney, Agent, or Firm*—Saliwanchik, Lloyd & Saliwanchik

[57] ABSTRACT

The subject invention pertains to quinolinesulfonamides. The subject compounds can be used to treat disease states, such as those that are associated with proteins that mediate cellular activity, for example, by inhibiting phosphodiesterase IV (PDE IV) or tumor necrosis factor (TNF). The invention also pertains to methods of treating disease states, including those states capable of being modulated by inhibition of PDE IV or TNF.

28 Claims, No Drawings

QUINOLINE SULFONAMIDES AND THEIR THERAPEUTIC USE

FIELD OF THE INVENTION

The present invention relates to novel quinolines, and to their formulation and use as pharmaceuticals.

BACKGROUND OF THE INVENTION

Japanese Patent Publication 2-184673 discloses quinolinesulphonamides.

U.S. Pat. No. 4,910,193 discloses quinolinesulphonamides, in which the sulphonamide nitrogen is substituted by a variety of bridged saturated ring systems, as medicaments suitable for the treatment of serotonin-induced gastrointestinal disturbances.

U.S. Pat. No. 4,857,301 and U.S. Pat. No. 5,340,811 disclose quinolinesulphonamides in the treatment of asthma, respectively as bronchodilators and as anti-allergic compounds.

Phosphodiesterases (PDE) and Tumour Necrosis Factor (TNF), their modes of action and the therapeutic utilities of inhibitors thereof, are described in WO-A-9636595. WO-A-9636596 and WO-A-9636611, the contents of which are incorporated herein by reference. The same documents disclose sulphonamides having utility as PDE and TNF inhibitors.

SUMMARY OF THE INVENTION

This invention is based on the discovery of novel compounds that can be used to treat disease states, for example disease states associated with proteins that mediate cellular activity, for example by inhibiting tumour necrosis factor and/or by inhibiting phosphodiesterase IV. According to the invention, the novel compounds are of formula (i):

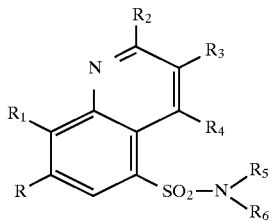

(i)

wherein R is H, halogen or alkyl;

$R_1$ represents OH, alkoxy optionally substituted with one or more halogens, or thioalkyl, $R_2$, $R_3$ and $R_4$ are the same or different and are each H, $R_7$, $OR_{11}$, $COR_7$, $C(=NOR_7)R_7$, alkyl-$C(=NOR_7)R_7$, alkyl-$C(=NOH)R_7$, $C(=NOH)R_7$, halogen, $CF_3$, CN, $CO_2H$, $CO_2R_{11}$, $CONH_2$, $CONHR_7$, $CON(R_7)_2$, $NR_9R_{10}$ or $CONR_{12}R_{13}$ where $NR_{12}R_{13}$ is a heterocyclic ring (such as morpholine or piperidine) optionally substituted with one or more $R_{15}$;

$R_5$ represents H, arylalkyl, heteroarylalkyl, $S(O)_mR_{11}$ or alkyl optionally substituted with one or more substituents chosen from hydroxy, alkoxy, $CO_2R_8$, $SO_2NR_{12}R_{13}$, $CONR_{12}R_{13}$, CN, carbonyl oxygen, $NR_9R_{10}$, $COR_{11}$ and $S(O)_nR_{11}$;

$R_6$ represents aryl, heteroaryl, arylalkyl or heteroarylalkyl;

in $R_5$ and/or $R_6$, the aryl/heteroaryl portion is optionally substituted with one or more substituents alkyl-$R_{14}$ or $R_{14}$;

$R_7$ represents $R_{11}$ optionally substituted at any position with (one or more) $R_{16}$;

$R_8$ represents H, alkyl, cycloalkyl, arylalkyl, heteroarylalkyl or heterocycloalkyl;

$R_9$ represents H, aryl, heteroaryl, heterocyclo, alkyl, cycloalkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl or alkylsulphonyl;

$R_{10}$ represents H, aryl, heteroaryl, heterocyclo, alkyl, cycloalkyl, arylalkyl, heteroarylalkyl or heterocycloalkyl;

$R_{11}$ represents alkyl, cycloalkyl, aryl, heteroaryl, heterocyclo, arylalkyl, heteroarylalkyl or heterocycloalkyl;

$R_{12}$ and $R_{13}$ are the same or different and are each H or $R_{11}$, or $NR_{12}R_{13}$ represents a heterocyclic ring as defined above;

$R_{14}$ represents alkyl (optionally substituted by one or more halogens), cycloalkyl, aryl, heteroaryl, heterocyclo, hydroxy, alkoxy (optionally substituted by one or more halogens), thioalkyl, aryloxy, heteroaryloxy, heterocycloxy, arylalkyloxy, heteroarylalkyloxy, heterocycloalkyloxy, $CO_2R_8$, $CONR_{12}R_{13}$, $SO_2NR_{12}R_{13}$, halogen, —CN, —$NR_9R_{10}$, $COR_{11}$, $S(O)_nR_{11}$, or (where appropriate) carbonyl oxygen;

$R_{15}$ represents alkyl, arylalkyl or heteroarylalkyl;

$R_{16}$ represents alkyl, OH, $OR_{11}$, $NR_9R_{10}$, CN, $CO_2H$, $CO_2R_{11}$, $CONR_{12}R_{13}$ or $COR_{11}$, m represents 1–2; and n represents 0–2;

and pharmaceutically-acceptable salts.

Combinations of substituents and/or variables are only permissible if such combinations results in stable compounds.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O- group in which the alkyl group is as previously described. Aryloxy means an aryl-O- group in which the aryl group is as defined below. Heteoaryloxy means a heteroaryl-O- group and heterocyclooxy means a heterocyclo-O- group in which the heteroaryl and heterocyclo group are as defined below. Alkylamino means an alkyl-N- group in which the alkyl group is as previously defined, arylamino means aryl-N- and heteroarylamino means an heteroaryl-N- group (aryl and heteroaryl defined below). Thioalkyl means an alkyl-S-group. Cycloalkyl includes a non-aromatic cyclic or multicyclic ring system of about 3 to 10 carbon atoms. The cyclic alkyl may optionally be partially unsaturated. Aryl indicates carboxylic radicals containing about 6 to 10 carbon atoms. Arylalkyl means an aryl-alkyl- group wherein the aryl and alkyl are as described herein. Heteroarylalkyl means a heteroaryl-alkyl group and heterocycloalkyl means a heterocyclo-alkyl group. Alkyl carbonyl means an alkyl-CO- group in which the alkyl group is as previously described. Arylcarbonyl means an aryl-CO- group in which the aryl group is as previously described. Heteroarylcarbonyl means a heteroaryl-CO- group and heterocyclocarbonyl means a heterocyclo-CO- group. Arylsulphonyl means an aryl-$SO_2$- group in which the aryl group is as previously described. Heteroarylsulphonyl means a heteroaryl-$SO_2$- group and heterocyclosulphonyl means a hetercyclo-$SO_2$- group. Alkoxycarbonyl means an alkyloxy-CO- group in wich the alkoxy group is as previously desribed. Alkylsulphonyl means an alkyl-$SO_2$- group in which the alkyl group is as previously described. Carbonyl oxygen means a —CO— group. It will be appreciated that a carbonyl oxygen can not be a substituent on an aryl or heteroaryl ring. Carbocyclic ring means about a 5 to about a 10 membered monocyclic or multicyclic ring system which may saturated or partially unsaturated. Heterocyclo ring means about a 5 to about a 10 membered monocyclic or multicyclic ring system (which may saturated or partially unsaturated) wherein one or more of the atoms in the ring system is an element other than carbon chosen from amongst nitrogen, oxygen or sulphur atoms. Examples include morpholine and piperidine. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur; if desired, a N atom may be in the form of an N-oxide. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Halogen means fluorine, chlorine, bromine or iodine.

Compounds of the invention are useful for the treatment of TNF mediated disease states, "TNF mediated disease or disease states" means any and all disease states in which TNF plays a role, either by production of TNF itself, or by TNF causing another cytokine to be released, such as but not limited to IL-1 to IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including: asthma, chronic bronchitis, chronic obstructive airways disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpora nephritis, joint inflammation, arthritis, rheumatoid arthritis and other arthritic conditions such as rhuematoic spondylitis and osteroarthritis, septic shock, sepsis, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. PDE IV inhibitors may be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$ etc. m and n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction sequence. Suitable protecting groups for such functionality will be apparent to those skilled in the art. For specific details, see Protective Groups in Organic Synthesis, Wiley Interscience, TW Greene. Thus the process for preparing compounds of formula (i) in which $R_3$ contains an —OH comprises of deprotecting (for example by hydrogenolysis or hydrolysis) a compound of formula (i) in which $R_3$ contains an appropriate —OP wherein P represents a suitable protecting group (e.g. benzyl or acetate).

It will be appreciated that where a particular stereoisomer of formula (i) is required, this may be obtained by conventional resolution techniques such as high performance liquid chromatography or the synthetic processes herein described may be performed using the appropriate homochiral starting material.

A process for the preparation of a compound of formula (i) comprises reaction of an appropriate sulphonyl chloride of formula (ii) with a suitable amine of formula (iii)

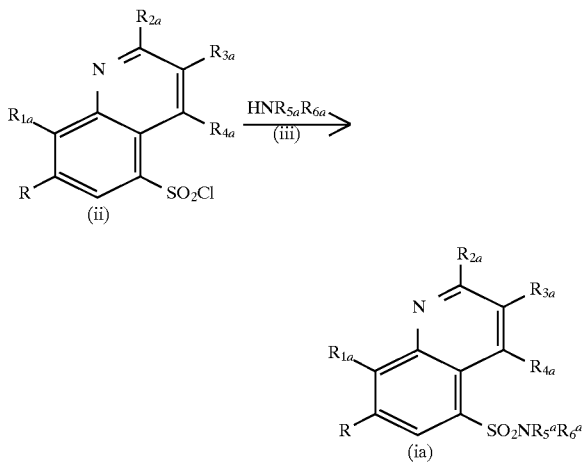

wherein $R_{1a}$ represents $R_1$ as defined in relation to formula (i) or a group convertible to $R_1$ and $R_{2a}$–$R_{6a}$ similarly represent $R_2$–$R_6$ or groups convertible to $R_2$–$R_6$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$ and/or converting any group $R_{4a}$ to $R_6$. The reaction of a sulphonyl chloride of formula (ii) which an amine of formula (iii) may be carried out under any suitable conditions known to those skilled in the art. Preferably, the reaction is carried out in the presence of a suitable base, for example an amine such as triethylamine, preferably in an appropriate solvent such as dichloromethane. In some cases a stronger base, such as sodium hydride, and a polar solvent such as dimethylformamide, will be required.

Sulphonyl chlorides of formula (ii) are either commercially available, previously described compounds or are prepared using standard procedures known to those skilled in the art. For example, a sulphonyl chloride of formula (ii) is conveniently prepared from the appropriate sulphonic acid (iv).

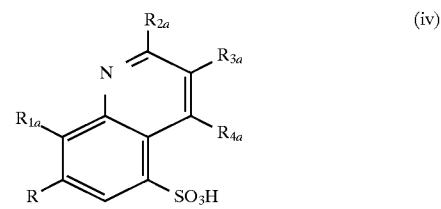

by treatment with a suitable agent such as thionyl chloride or oxalyl chloride. Alternatively, a sulphonyl chloride of formula (II) may be prepared by sulphonylation of an appropriate quinoline of formula (v)

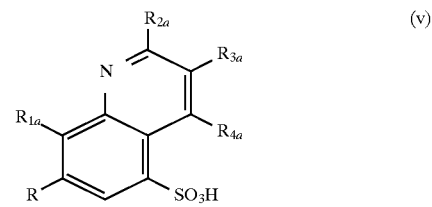

with a suitable sulphonylating agent such as chlorosulphonic acid.

Compounds of formula (v) are either commercially-available, previously described compounds or are prepared using standard procedures known to those skilled in the art. For example quinolines of formula (v) may be conveniently prepared by a Skraup reaction (Z. H. Skraup, Ber. 13:2086 (1880)).

A compound of formula (ia) may also be prepared by reaction of a sulphonyl chloride of formula (ii) with an amine of the formula $H_1NR_{6a}$ (vi), to provide a compound of formula (ia) in which $R_{5a}$ is H, followed by reaction with an appropriate agent of formula $R_{5a}Y$ (vii), wherein $R_{1a}$–$R_{6a}$ are as defined above and Y represents a suitable leaning group such as halogen. The reaction of a sulphonyl chloride of formula (ii) with an amine of formula (vi) may be carried out under any suitable conditions known to those skilled in the art. Preferably, the reaction is carried out in the presence of a suitable base, for example an amine such as triethylamine, preferably in an appropriate solvent such as dichloromethane. In some cases, a stronger base such as sodium hydride, and a polar solvent such as dimethylformamide, may be required.

The reaction of a compound of formula (ia) in which $R_{1a}$ is H with an agent of formula (vii) may be carried out under any suitable conditions known to those skilled in the art. Preferably, the reaction is carried out using an appropriate base, such as sodium hydride, preferably in an appropriate solvent such as dimethylformamide. Agents of formula (vii) are either commercially available or are prepared using standard procedures known to those skilled in the art. Agent (vii) can be an alkylating agent such as propyl bromide, an acylating agent such as benzoyl chloride or a sulphonylating agent such as methanesulphonyl chloride.

Amines of formulae (iii) and (vi) are commercially available, previously described compounds or are prepared using standard procedures known to those skilled in the art.

A compound of formula (i) may also be prepared by interconversion of other compounds of formula (i). For example, a compound in which $R_3$ contains an alkoxy group may be prepared by appropriate alkylation of a compound in which $R_3$ contains a hydroxy group.

Compounds in which $R_2$–$R_4$ contain a CO-alkyl, CO-aryl, CO-heteroaryl, CO-alkylaryl, CO-alkylheteroaryl or CO-alkylheterocyclo group may be prepared from compounds in which $R_2$–$R_4$ contain a CN group, by addition of a suitable organometallic agent (such as a Grignard reagent).

By way of further example, compounds in which $R_2$–$R_4$ contain an oxime may be prepared from compounds in which $R_2$–$R_4$ contain a carbonyl group. This transformation may be carried out using any appropriate standard conditions known to those skilled in the art. Compounds of formula (i) in which $R_2$–$R_4$ contain a carbonyl group may be reduced using standard conditions known to those skilled in the art (for example with sodium borohydride in an appropriate solvent) to provide compounds in which $R_2$–$R_4$ contains an alcohol group. Compounds in which $R_2$–$R_4$ is alkyl may be prepared by reduction of compounds in which $R_2$–$R_4$ is CO-alkyl using standard conditions known to those skilled in the art (for example hydrazine hydrate in the presence of a suitable base in an appropriate solvent). Other transformations may be carried out on compounds of formula (i) in which $R_2$–$R_4$ contains a carbonyl group. Such transformations include, but are not limited to, reductive amination and alkylation. Any of the above transformations may be carried out either at the end of the synthesis or on an appropriate intermediate.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitable be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspensions in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressing, gels, gel sticks, spray and aerosols, and may contain appropriate conventional additives such as preservations, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations will known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

Intermediate 1 8-Methoxyquinoline-5-(N-benzyl) sulphonamide

Triethylamine (0.38 ml) was carefully added to a suspension of 8-methoxyquinoline-5-sulphonyl chloride (203 mg) in dichloromethane (10 ml) at 0° C. under nitrogen. Benzylamine (90 μl) was then added and the mixture stirred for 30 minutes at 0° C. and 16 hours at room temperature. The reaction was diluted with dichloromethane (30 ml), washed with water (15 ml) and saturated aqueous sodium chloride (20 ml). The organic layer was dried over magnesium sulphate, filtered and the filtrate evaporated in vacuo. The residue was purified by column chromatography on silica gel eluting with 2% methanol in dichloromethane to yield the titled compound as a white solid (135 mg) Mp 150°–151° C.

EXAMPLE 1

8-Methoxyquinoline-5-(N-benzyl-N-methanesulphonyl)sulphonamide

Sodium hydride (120 mg, 60% dispersion in oil) was added to a solution of 8-methoxyquinoline-5-(N-benzyl) sulphonamine (120 mg) in anhydrous DMF (3 ml) at 0° C. under nitrogen. The resultant mixture was stirred for 20 minutes and then treated with methanesulphonyl chloride (34 μl). The reaction was stirred for one hour at 0° C. and 18 hours at room temperature. Water (1 ml) was carefully added and the solvent evaporated in vacuo. The residue was partitioned between dichloromethane (20 ml) and saturated aqueous sodium hydrogen carbonate solution (10 ml). The aqueous layer was extracted with dichloromethane (10 ml). The organic extracts were combined and washed with saturated aqueous sodium chloride (10 ml), dried over magnesium sulphate, filtered and the filtrate evaporated in vacuo. The residue was purified by column chromatography on silica gel eluting with 10% ethyl acetate in dichloromethane to yield the title compound as a white solid (99 mg) after trituration with diethyl ether.

TLC $R_f$ 0.45 (5% methanol in dichloromethane) Mp 157°–158° C.

EXAMPLE 2

8-Methoxyquinoline-5-(N-benzyl-N-propyl) sulphonamide

The title compound was obtained as a colourless gum (250 mg) from 8-methoxyquinoline-5-(N-benzyl) sulphonamide and bromopropane using a similar procedure to that described in Example I.

TLC $R_5$ 0.1 (50% ethyl acetate in hexane).

Assay methods

The assays used to confirm the phosphodiesterase IV inhibitory activity of compounds of formula (i) are standard assay procedures as disclosed by Schilling et al., Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human peripheral blood mononuclear cells (PMBC's) is measured as follows. PBMC's are prepared from freshly taken blood or "Buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, Br. J. Pharmacol. 111:811 (1994) and Br. J. Pharmacol. 110:416 (1993). Activity in a lung model is measured using the procedures described by Kallos and Kallos, Int. Archs. Allergy Appl. Immunol. 73:77 (1984), and Sanjar et al., Br. J. Pharmacol. 99:679 (1990).

An additional lung model, which allows measurement of inhibition of the early and late-phase asthmatic responses and also the inhibition of airway hyperreactivity, is described by Broadley et al, Pulmonary Pharmacol. 7:311 (1994), J. Immunological Methods 190:51 (1996) and British J. Pharmacol. 116:2351 (1995).

Abbreviations

LPS Lipopolysaccharide (endotoxin)

ELISA Enzyme link immunosorbent assay

We claim:
1. A compound of the general formula (i)

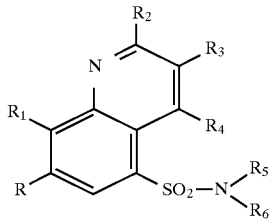

wherein
R is selected from the group consisting of H, halogen, and alkyl;
$R_1$ is selected from the group consisting of OH, alkoxy optionally substituted with one or more halogens, and thioalkyl;
$R_2$, $R_3$, and $R_4$ are the same or different and are each selected from the group consisting of H, $R_7$, $OR_{11}$, $COR_7$, $C(=NOR_7)R_7$, alkyl-$C(=NOR_7)R_7$alkyl-C$(=NOR)R_7$, $C(=NOH)R_7$, halogen, $CF_3$, CN, $CO_2H$, $CO_2R_{11}$, $CONH_2$, $CONHR_7$, $CON(R_7)_2$, $NR_9R_{10}$, and $CONR_{12}R_{13}$ where $NR_{12}R_{13}$ is a heterocyclic ring optionally substituted with one or more $R_{15}$;
$R_5$ is selected from the group consisting of arylalkyl, heteroarylalkyl, $S(O)_mR_{11}$, and alkyl optionally substituted with one or more substituents selected from the group consisting of hydroxy, alkoxy, $CO_2R_8$, $SO_2NR_{12}R_{13}$, $CONR_{12}R_{13}$, CN, $NR_9R_{10}$, $COR_{11}$, and $S(O)_nR_{11}$;
for $R_5$ and/or $R_6$, the aryl/heteroaryl portion is optionally substituted with one or more substituents alkyl-$R_{14}$ or $R_{14}$;
$R_6$ is selected from the group consisting of aryl, heteroaryl, arylalkyl, and heteroarylalkyl;
$R_7$ represents $R_{11}$ optionally substituted at any position with one or more $R_{16}$;
$R_8$ is selected from the group consisting of H, alkyl, cycloalkyl, arylalkyl, heteroarylalkyl, and heterocycloalkyl;
$R_9$ is selected from the group consisting H, aryl, heteoaryl, heterocyclo, alkyl, cycloalkyl, arylalkyl, heteroarylalkyl, heterocyclalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl, and alkylsulphonyl;
$R_{10}$ is selected from the group consisting of H, aryl, heteroaryl, heterocyclo, alkyl, cycloalkyl, arylalkyl, heteroarylalkyl, and heterocycloalkyl;
$R_{11}$ is selected from the group consisting of alkyl, cycloalkyl, aryl, heteroaryl, heterocyclo, arylalkyl, heteroarylalkyl, and heterocycloalkyl;
$R_{12}$ and $R_{13}$ are the same or different and are each selected from the group consisting of H and $R_{11}$, or $NR_{12}R_{13}$ represents a heterocyclic ring as defined above;
Rhd 14is selected from the group consisting of alkyl (optionally substituted by one or more halogens), cycloalkyl, aryl, heteroaryl, heterocyclo, hydroxy, alkoxy (optionally substituted by one or more halogens), thioalkyl, aryloxy, heteroaryloxy, heterocyclooxy, arylalkyloxy, heteroarylalkyloxy, heterocycloalkyloxy, $CO_2R_4$, $CONR_{12}R_{13}$, $SO_2NR_{12}R_{13}$, halogen, —CN, —$NR_9R_{10}$, $COR_{11}$, $S(O)_nR_{11}$, and carbonyl oxygen;

$R_{15}$ is selected from the group consisting of alkyl, arylalkyl, and heteroarylalkyl;
$R_{16}$ is selected from the group consisting of alkyl, OH, $OR_{11}$, $NR_9R_{10}$, CN, $CO_2H$, $CO_2R_{11}$, $CONR_{12}R_{13}$, and $COR_{11}$;
m is an integer of up to 2; and
n=0–2;
or a pharmaceutically acceptable salt thereof.

2. The compound, according to claim 1, wherein R is H or halogen.

3. The compound, according to claim 1, wherein $R_1$ is alkoxy optionally substituted with one or more halogens.

4. The compound, according to claim 1, wherein $R_2$, $R_3$, and $R_4$ are the same or different and are each selected from the group consisting of H, $CF_3$, $COR_7$, $C(=NOR_7)R_7$, $C(=NOH)R_7$, CN, $R_7$, alkyl-$C(=NOH)_7$, and alkyl-C$(=NOR_7)R_7$.

5. The compound, according to claim 1, wherein $R_5$ is selected from the group consisting of arylalkyl, heteroarylalkyl, $S(O)_mR_{11}$, and alkyl.

6. The compound, according to claim 1, wherein $R_6$ is arylalkyl or heteroaryl in which the aryl and heteroaryl portions may be optionally substituted with one or more substituents alkyl-$R_{14}$ or $R_{14}$.

7. The compound, according to claim 1, wherein:
R is H;
$R_1$ is optionally-substituted alkoxy;
$R_2$, $R_3$, and $R_4$ are independently selected from the group consisting of H, $R_7$, and alkyl-$R_7$;
$R_7$ is selected from the group consisting of H, OH, alkoxy, aryloxy, heteroaryloxy, heterocyclooxy, arylalkoxy, heteroarylalkoxy, heterocycloalkyoxy, alkylamino, $CF_3$, and $R_{11}$;
$R_8$ is selected from the group consisting of H, alkyl, arylalkyl, heteroarylalkyl, and heterocycloalkyl;
$R_9$ is not cycloalkyl;
$R_{10}$ is not cycloalkyl;
$R_{11}$ is not cycloalkyl; and
$R_{14}$ is not alkyl, substituted alkoxy, thioalkyl, or cycloalkyl.

8. The compound, according to claim 1, which is 8-methoxyquinoline-5-(N-benzyl-N-methanesulphonyl)sulphonamide.

9. The compound, according to claim 1, which is 8-methoxyquinoline-5-(N-benzyl-N-propyl)sulphonamide.

10. The compound, according to claim 1, which is in the form of an enantiomer or mixers of enantiomers.

11. A pharmaceutical composition for therapeutic use comprising a compound of claim 1 and a pharmaceutically-acceptable carrier or excipient.

12. A method for treating a disease state capable of being modulated by inhibition of phosphodiesterase IV or Tumour Necrosis Factor, wherein said method comprises administering an effective amount of a compound of claim 1.

13. The method, according to claim 12, wherein said disease state is a pathological condition associated with the function of phosphodiesterase IV, eosinophil accumulation, or a function of the eosinophil.

14. The method, according to claim 13, wherein said pathological condition is selected from the group consisting of asthma, chronic bronchitis, chronic obstructive airways disease, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis or other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke, and intermittent claudication.

15. The method, according to claim 13, wherein said pathological condition is selected from the group consisting of chronic bronchitis, allergic rhinitis, and adult respiratory distress syndrome.

16. The method, according to claim 12, wherein said disease state is capable of being modulated by TNF inhibition.

17. The method, according to claim 16, wherein said disease state is an inflammatory disease or autoimmune disease.

18. The method, according to claim 17, wherein said disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption disease, reperfusion injury, graft vs host reaction, allograft rejection, malaria, myalgias, HIV, AIDS, ARC, cachexia, Crohn's disease, ulcerative colitis, pyresis, systemic lupus erythematosis, multiple sclerosis, type I diabetes mellitus, psoriasis, Bechet's disease, anaphylactoid purpura nephritis, chronic glomerulonephritis, inflammatory bowel disease, and leukemia.

19. The method, according to claim 18, wherein said disease state is asthma.

20. The method, according to claim 14, wherein said pathological condition is asthma.

21. The method, according to claim 18, wherein said disease state is selected from the group consisting of acute respiratory distress syndrome, pulmonary inflammatory disease, and pulmonary sarcoidosis.

22. The method, according to claim 18, wherein said disease state is joint inflammation.

23. The method, according to claim 13, wherein said disease state is a disease or disorder of the brain.

24. The method, according to claim 23, wherein said disease state is selected from the group consisting of brain trauma, stroke, ischaemia, Huntingdon's disease, and tardive dyskinesia.

25. The method, according to claim 16, wherein said disease state is a yeast or fungal infection.

26. A method for providing gastroprotection, wherein said method comprises administering an effective amount of a compound of claim 1.

27. A method for providing an analgesic, an anti-tussive, or an anti-hyperalgesic in the treatment of neurogenic inflammatory disease associated with inflammation and pain, wherein said method comprises administering an effective amount of a compound of claim 1.

28. A method for treating asthma which comprises administering an effective amount of a compound of claim 1, in coadministration with a drug selected from the group consisting of bronchodilators, steroids, and xanthines.

* * * * *

UNITED STATES PATENT AND TRADEMARK OFFICE
CERTIFICATE OF CORRECTION

PATENT NO. : 5,834,485
DATED : November 10, 1998
INVENTOR(S) : Hazel Joan Dyke and John Gary Montana It is certified that error appears in the above-identified patent and that said Letters Patent is hereby corrected as shown below:

Column 11, line 21: "$R_7$alkyl-C (=NOR)$R_7$" should read --$R_7$, alkyl-C (=NOH)$R_7$--;

line 27: "$S(O)_m R_{11}$," should read --$S(O)_m R_{11}$,--;

line 31: "$S(O)_n R_{11}$," should read --$S(O)_n R_{11}$,--;

line 44: "heteoaryl," should read --heteroaryl,--;

line 45: "heterocyclalkyl" should read --heterocycloalkyl--;

line 59: "Rhd 14is" should read --$R_{14}$ is--;

line 65: "$CO_2 R_4$," should read --$CO_2 R_8$,--; and line 67: "$S(O)_n R_{11}$," should read --$S(O)_n R_{11}$,--.

Column 12, line 20: "$S(O)_m R_{11}$," should read --$S(O)_m R_{11}$,--;

line 33: "heterocycloalkyoxy" should read --heterocycloalkoxy--; and line 49: "mixers" should read --mixture--.

UNITED STATES PATENT AND TRADEMARK OFFICE
CERTIFICATE OF CORRECTION

PATENT NO. : 5,834,485
DATED : November 10, 1998
INVENTOR(S) : Hazel Joan Dyke and John Gary Montana It is certified that error appears in the above-identified patent and that said Letters Patent is hereby corrected as shown below:

Column 13, line 24: "disease" should read --diseases--; and line 27: "erythematosis" should read --erythematosus--.

Signed and Sealed this

Fourth Day of May, 1999

Attest:

Q. TODD DICKINSON

*Attesting Officer*     *Acting Commissioner of Patents and Trademarks*